United States Patent [19]

Balani et al.

[11] Patent Number: 5,200,329
[45] Date of Patent: Apr. 6, 1993

[54] METHOD OF HYDROXYLATING 3-[(4,7-DICHLOROBENZOXAZOL-2-YL)METHYL]AMINO-5-ETHYL-6-METHYL-2-(1H)-PYRIDINONE BY INCUBATION WITH LIVER SLICES

[75] Inventors: Suresh K. Balani, Hatfield; Anthony D. Theoharides, Lansdale; Laura R. Kauffman, Jeffersonville, all of Pa.

[73] Assignee: Merck & Co., Inc., Rahway, N.J.

[21] Appl. No.: 850,008

[22] Filed: Mar. 10, 1992

Related U.S. Application Data

[63] Continuation of Ser. No. 771,963, Oct. 4, 1991, abandoned.

[51] Int. Cl.$^5$ .............................................. C12P 17/16
[52] U.S. Cl. ............................................................. 435/118
[58] Field of Search .................................. 435/118

[56] References Cited

PUBLICATIONS

Ratner, L. et al., "Complete nucleotide sequence of the AIDS virus", HTLV-III, Nature 313, 277 (1985).
Toh, H. et al., "Close structural resemblance . . .," EMBO Journal 4, 1267 (1985).
Power, M. D. et al., "Nucleotide Sequence of SRV-1," Science 231, 1567 (1986).
Pearl, L. H. et al., "A structural model for Retroviral Proteases," Nature 329, 351 (1987).
Paine, J. B., "A Convenient Synthesis of Nicotinate Esters . . .," J. Heterocyclic Chem. 24, 351 (1987).
Azri, S. et al., "Precision-Cut Liver Slices," In Vitro Toxicology 3, 309 (1990).
Smith, P. F. et al., "Dynamic Organ Culture of Precision Liver Slices . . .," Liver Slices for In Vitro Technology 36, 1367 (1985).
Krumdieck, C. L. et al., "A New Instrument for Rapid Preparation of Tissue Slices," Anal. Biochem. 104, 118 (1980).
Chapman, D. E. et al., "Metabolism and Covalent Binding of $^{14}$C-toluene by Human and Rat Liver Microsimal Fraction, Drug Metabolism and Disposition" 18, 929 (1990).
Goldman, M. et al., "Pyridinone derivatives: Specific HIV-1 reverse transcriptase inhibtiors with antiviral activities", Proc. Natl. Acad. Sci. 88, 6863 (1991).

Primary Examiner—Douglas W. Robinson
Assistant Examiner—S. Saucier
Attorney, Agent, or Firm—Roy D. Meredith; Charles M. Caruso

[57] ABSTRACT

Incubation of 3-[(4,7-dichlorobenzoxazol-2-yl)methyl]amino-5-ethyl-6-methyl-2-(1H)-pyridinone

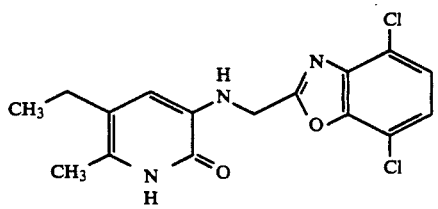

with a preparation from mammalian organ yields as biotransformation products the 5-(1-hydroxy)ethyl and 6-hydroxymethyl analogs. These products are useful in the prevention or treatment of infection by HIV and the treatment of AIDS.

2 Claims, No Drawings

METHOD OF HYDROXYLATING 3-[(4,7-DICHLOROBENZOXAZOL-2-YL)METHYL-]AMINO-5-ETHYL-6-METHYL-2-(1H)-PYRIDI-NONE BY INCUBATION WITH LIVER SLICES

This is a continuation of application Ser. No. 07/771,963, filed Oct. 4, 1991 now abandoned.

This case is related to Merck cases 18122, 18122IA, 18122IB, 18131, 18131IA, 18132, 18132IA, 18212, 18212IA, 18317, 18376, 18377, 18379, 18463, and 18465.

The present invention relates to a novel process for the preparation of compounds (Ia) and (Ib)

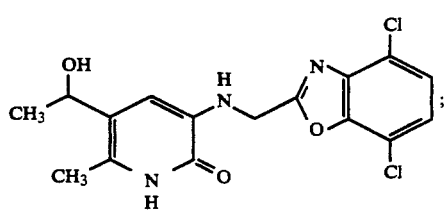

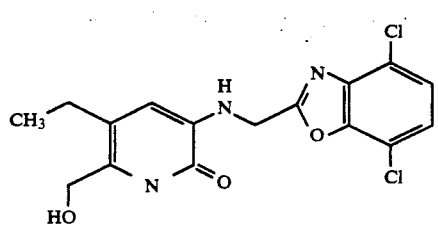

comprising incubation of compound (II), an inhibitor of the reverse transcriptase encoded by human immunodeficiency virus (HIV).

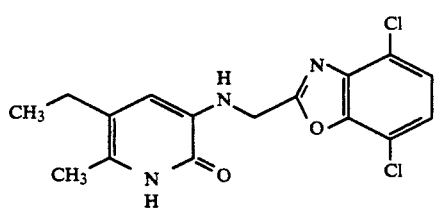

with a preparation from mammalian organ. Compounds (Ia) and (Ib) or the pharmaceutically acceptable esters thereof inhibit the reverse transcriptase encoded by HIV and are of value in the prevention of infection by HIV, the treatment of infection by HIV and the treatment of the resulting acquired immune deficiency syndrome (AIDS).

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

The nucleotide sequence of HIV shows the presence of a pol gene in one open reading frame [Ratner, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

The compounds prepared by the process of this invention are inhibitors of HIV reverse transcriptase. Since the compounds themselves are metabolites, they are better adapted as a pharmaceutical product. Further, the compounds of the present invention do not require bio-activation to be effective.

BRIEF DESCRIPTION OF THE INVENTION

The novel process of this invention comprises incubation of Compound II,

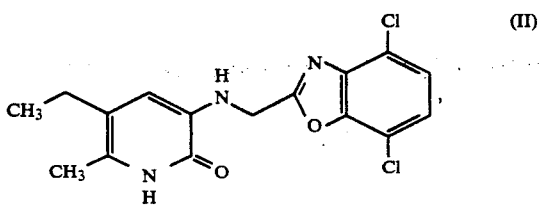

with a preparation from a mammalian organ, and isolation of the resulting biotransformation products, Compounds (Ia) and (Ib), in a conventional manner:

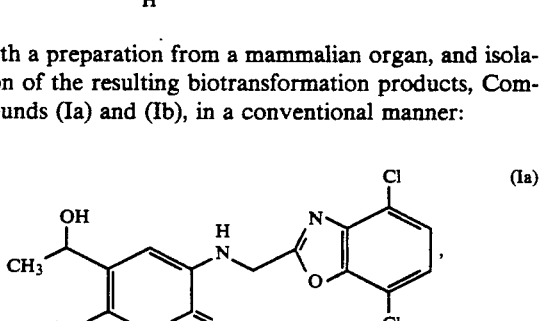

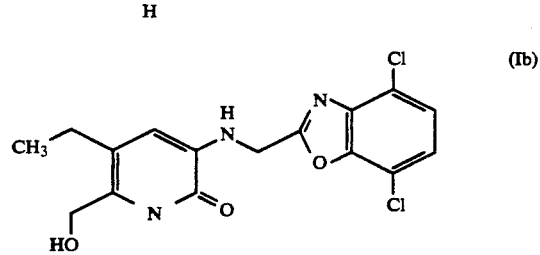

These compounds are useful in the inhibition of HIV reverse transcriptase, the prevention of infection by HIV, the treatment of infection by HIV and in the treatment of AIDS and/or ARC, either as a compound, pharmaceutically acceptable salt (when appropriate), hydrate, ester, pharmaceutical composition ingredient, whether or not in combination with other antivirals, anti-infectives, immunomodulators, antibiotics or vaccines.

DETAILED DESCRIPTION OF THE INVENTION AND PREFERRED EMBODIMENTS

The novel process of this invention comprises incubation of compound (II), with a preparation from mammalian organ, and isolation of the resulting biotransformation products, compounds (Ia) and (Ib), in a conventional manner:

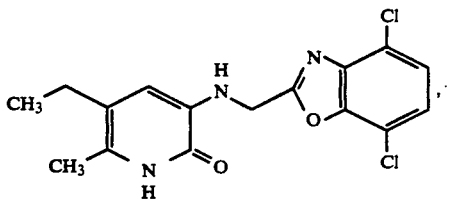

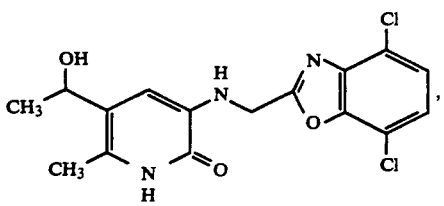

3-[(4,7-dichlorobenzoxazol-2-yl)methylamino]-5-(1-hydroxyethyl)-6-methylpyridin-2(1H)-one;

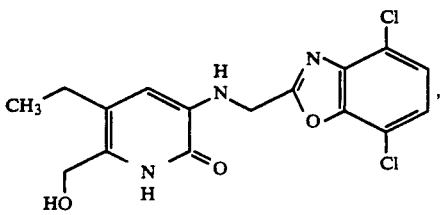

3-[(4,7-dichlorobenzoxazole-2-yl)methylamino]-5-ethyl-6-hydroxymethylpyridin-2(1H)-one.

In general, compounds (Ia) and (Ib), which are respectively the 5-(1-hydroxy)-ethyl and 6-hydroxymethyl oxidation products, can be produced by incubating an appropriate amount of substrate compound (II) with certain mammalian tissues or cell cultures in an aqueous medium suitable for enhancing the viability of the tissues or cells. Metabolite (Ia) and/or (Ib) may be produced by incubation of compound (II) with a preparation from mammalian organ containing: a) surgically derived specimens including liver, kidneys, lungs and skin, both from animals and human beings; b) prenatal and gestational tissues; c) cell cultures; d) subcellular fractions like microsomes, S9 and cytosol; and/or e) purified mixed function oxidases. These metabolites could also be formed in vivo in animals and human beings. The preferred tissue for production of compound (Ia) and (Ib) is liver, especially rat liver slices.

The appropriate amount of tissue or cell culture to be used with a given amount of substrate compound will vary with the particular type of culture used. An appropriate ratio of substrate compound (II) to be incubated with liver tissue (mg:g, wet weight) ranges from about 1:0.3 to 1:3.0, preferably 1:2.4. When using surgically derived specimens, especially liver, the specimen is preferably cut into slices with thickness ranging from about 100μ to 1000μ, and more preferably from about 250 to 400μ.

Aqueous media sufficient in amount and kind to keep the tissue or cells healthy in the incubation process should be used. These media are known and available in the art of drug metabolism and include various buffers and standard culture media with or without additives. A few examples of various culture media that may be employed are Williams' Medium E, Waymouth's Medium, Dulbecco's Medium, RPMI Medium and the like. Culture media can be replaced by general buffers such as phosphate buffers. Various additives that may be used to enhance the viable life of the cells and tissues are a) serum from bovine, horse, chicken, goat, sheep, rabbit and the like; b) HEPES or MOPS; c) gentamycin; and d) insulin, for example. A preferred medium for incubation of substrate compound (II) with rat liver slices is Williams' Medium E.

The material is incubated at a temperature between 35° and 39° C., preferably 37° C., and at a pH between 7.2 and 7.6, preferably 7.4, under an atmosphere of 0% to 5% carbon dioxide in oxygen, or air. The material is incubated for a period of time necessary to complete the oxidative biotransformation as monitored by HPLC (high performance liquid chromatography), usually for a period of about five hours when incubated with rat liver slices.

The biotransformation products (Ia) and (Ib) can be isolated and purified from the incubation mixture by extraction with a conventional solvent(s) or mixtures thereof, such as methylene chloride, ethyl acetate, acetonitrile, methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred recovery method is solvent extraction, particularly using ethyl acetate. A preferred purification method involves the use of chromatography, especially HPLC, using a bonded silica gel column. Eluant mixtures for chromatography can be composed of water and an organic solvent such as methanol, acetonitrile and the like, and may optionally include a small amount of base, such as ammonium bicarbonate, or an acid, such as trifluroacetic acid, phosphoric acid, or acidic ammonium acetate. A preferred eluant is composed of acetonitrile and water containing 0.1% ammonium bicarbonate and is run through the column with a linear gradient.

A process for making esters of (Ia) and/or (Ib) is also encompassed by the present invention. Such esters are those which would readily occur to the skilled artisan, and include, for example, $C_{1-4}$ alkyl esters. The biotransformed compound (Ia) of this invention has an asymmetric center and may occur as a racemate, racemic mixture, mixture of enantiomers, or as an individual enantiomer, with all enantiomeric forms being included in the present invention.

The compounds of the present inventions are useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of bodily fluids, bites, accidental needle stick, or exposure to patient blood during surgery.

EXAMPLE 1

Preparation of
3-[(4,7-dichlorobenzoxazol-2-yl)-methyl]amino-5-ethyl-
6-methyl-2(1H)-pyridinone, Compound II

Step A: Preparation of 2-amino-3,6-dichlorophenol

A yellow solution of 2,5-dichloro-6-nitrophenol (10.0 g, 48.0 mmol) in ethanol (200 mL) and acetic acid (13.8 mL) at 0° C. was catalytically reduced in the presence of 5% Platinum on charcoal (0.15 g) under an atmosphere of hydrogen (25 psi) for 1 hour in a Parr hydrogenator. The resultant colorless solution was filtered and concentrated under reduced pressure (15 torr). The residue was then dried under high vacuum (0.02 torr) overnight to yield 8.52 g (100%) of 2-amino-3,6-dichlorophenol.

Step B: Preparation of 2-chloromethyl-4,7-dichlorobenzoxazole

To a solution of 2-amino-3,6-dichlorophenol (23. g, 134 mmol) in methylene chloride (270 mL), solid ethyl chloroiminoacetate hydrogen chloride (31.9 g, 202 mmol) was added. The resultant slurry was stirred at room temperature overnight, then filtered through a plug of Celite, and concentrated under reduced pressure (15 torr). The solid residue was subjected to column chromatography on silica gel (elution with chloroform). Collection and concentration of appropriate fractions yielded 26.6 g (86%) of 2-chloromethyl-4,7-dichlorobenzoxazole.

Step C: Preparation of 3-[2-(4,7-dichlorobenzoxazolyl)methyl]amino-5-ethyl-6-methyl-2(1H)-pyridinone A mixture of 3-amino-5-ethyl-6-methylpyridine-2-one (0.93 g, 6.1 mmol, see Example 2), 2-chloromethyl-4,7-dichlorobenzoxazole (1.45 g, 6.1 mmol), diisopropylethylamine (1.06 mL, 6.1 mmol) in acetonitrile (30 mL) was reluxed under an atmosphere of nitrogen for 20 hours. The resultant mixture was cooled at 0° C. The solid precipitated was filtered and subjected to column chromatography on silica gel (elution with 4% methanol in chloroform). Collection and concentration of appropriate fractions provided 0.76 g of a white solid which was then recrystallized from ethanol to yield 0.66 g (31%) of 3-[2-(4,7-dichlorobenzoxazolyl)methyl]amino-5-ethyl-6-methyl-2(1H)-pyridinone.

Anal. Calcd. for $C_{16}H_{15}Cl_2N_3OS$: C, 54,56; H, 4.29; N, 11.93 Found C, 54.43; H, 4.12; N, 11.89

EXAMPLE 2

Preparation of 3-amino-5-ethyl-6-methyl-2-(1H) pyridinone

Step A: Preparation of 5-ethyl-6-methyl-3-nitro-2-(1H)-pyridinone

A mixture of 2-ethyl-3-oxobutanal, sodium salt (7.5 g, 55 mmol), nitroacetamide (6.6 g, 63 mmol), aqueous piperidinium acetate (4.4 mL) [prepared from glacial acetic acid (42 mL), water (100 mL) and piperidine (72 mL)] in water (45 mL) was stirred at room temperature for 22 hours. The yellow precipitate was collected by filtration and air dried to yield 8.0 g (80%) of 5-ethyl-6-methyl-3-nitro-2-(1H)-pyidinone.

Step B: Preparation of 3-amino-5-ethyl-6-methyl-2-(1H)-pyridinone

A yellow solution of the 5-ethyl-6-methyl-3-nitro-2-(1H)-pyridinone (10 g, 55 mmol) in a mixture of methanol and tetrahydrofuran (100 mL, 1:1 v/v) was reduced catalytically in the presence of 7% palladium on charcoal (0.7 g) under an atmosphere of hydrogen (50 psi) at room temperature over a period of 3.5 hours. The resultant mixture was filtered through a small pad of Celite. The filtrate was concentrated under reduced pressure (15 torr) to provide 5.7 g (68%) of the corresponding aminopyridone.

EXAMPLE 3

Incubation With Rat Liver Slices

Compound (II) (14.3 μmol) was incubated with rat liver slices (12 g wet weight, 250–400μ thick, about 1.2 cm wide) in 100 ml of Williams' Medium E at pH 7.4 and at 37° C. in an atmosphere of 95% oxygen and 5% carbon dioxide. After five hours the incubation mixture was extracted with ethyl acetate. The extract was concentrated to dryness and reconstituted in methanol, followed by preparative reverse-phase HPLC for isolation and purification of the metabolites. Two HPLC peaks (Ia and Ib) were selected for structural characterisation.

EXAMPLE 4

Structural Determination: FAB/MS and NMR

The compounds of interest—Ia and Ib—were characterized by FAB-Mass spectrometry and Proton NMR spectroscopy. Low Resolution FAB-Mass spectral analysis in glycerol or thioglycerol matrix gave $(M+H)^+$ peak at m/z 368, indicating the metabolites to be hydroxy derivatives of the parent compound (II). The NMR spectrum of Ia showed the following key changes in the 5-ethyl group resonances: the 5-α- and 5-β-proton signals were shifted to 4.86 ppm (multiplet) and 1.34 ppm (doublet), relative to those of the parent compound at 2.42 ppm (quartet) and 1.14 ppm (triplet), respectively. Based on NMR and Mass spectral data, the structure of Ia was assigned as the 5-α-hydroxyethyl analog. Ib similarly showed an NMR spectral shift for the 6-methyl protons at 4.50 ppm (singlet) relative to that for the parent compound at 2.21 ppm (singlet), assigning the structure of this metabolite as the 6-hydroxymethyl derivative of the parent compound.

EXAMPLE 5

Incubation With Human Liver Slices

Compound (II) (2.85 μmol) was incubated with liver slices (1.25 g wet weight) from a human donor (female, 74 years) in 20 ml of Williams' Medium E at 37° C. under an atmosphere of 5% $CO_2$ in air for four hours. The metabolites were extracted into ethyl acetate followed by evaporation of the solvent. The residue was reconstituted in methanol and compared on HPLC with an extract of rat liver slice incubation of compound (II). The HPLC effluents were monitored by a UV-diode array detector, and fractionated for liquid scintillation spectrophotometry. The HPLC comparisons of UV and radioactivity profiles indicated the formation of Ia and Ib in the human liver slices incubation.

EXAMPLE 6

Reverse Transcriptase Assay

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C).oligo $d(G)_{12-18}$. The inhibitor of the present invention inhibits this incorporation.

Thirty uL of a reaction mixture containing equal volumes of: 500 mM Tris.HCl (pH 8.2), 300 mM $MgCl_2$, 1200 mM KCl, 10 mM DTT, 400 µg/mL poly r(c).oligo d(G) [prepared by dissolving 1.5 mg (25 U) poly r(C).oligo d(G) in 1.5 ml sterile distilled $H_2O$ and diluting to 400 µg/ml], 0.1 µCi/µl [$^3$H] dGTP, 160 µM dGTP, was added to 10 µl sterile distilled $H_2O$, and 2.5 µl of potential inhibitor. An aliquot of 10 µL of 5 nM purified HIV $RT_R$ was added to initiate thereaction. The mixture was incubated at 37° C. for 45 minutes.

After incubation is complete, the tubes were cooled in ice for 5 minutes. Ice-cold 13% TCA containing 10 mM $NaPP_i$ (200 µl) are added and the mixture incubated on ice for 30 minutes. The precipitated cDNA is removed by filtration using presoaked glass filters [TCA, $NaPP_i$]. The precipitate is then washed with 1N HCl, 10 mM $NaPP_i$.

The filter discs are then counted in a scintillation counter.

Under these conditions [dGTP] and poly r(C).oligo $d(G)_{12-18}$ each are approximately equal to the appropriate Km value. Approximately 5–6,000 cpm of [$^3$H] GMP are incorporated into acid-precipitable material. The RT reaction is concentration- and time-dependent. DMSO (up to 5%) does not affect enzyme activity. The calculated $IC_{50}$ value for the compounds (Ia) and (Ib) of this incertion are as follows:

| Compound | $IC_{50}$ (µM) | Nature |
|---|---|---|
| Ia | 1.05 | Synthetic Racemate |
| Ib | 0.014 | Synthetic |
| II | 0.020 | Synthetic |

EXAMPLE 7

3-[2-(4,7-Dichlorobenzoxazol-2-yl)methylamino]-5-ethyl-6-hydroxymethylpridin-2(1H)-one, (Ib)

Step A: Preparation of 3-nitro-5-ethyl-6-benzyloxymethylpyridin-2(1H)-one

Benzyloxy acetyl chloride (14.2 mL, 0.09 mol) in dry tetrahydrofuran (10 mL) was added dropwise to a solution of 1-(N-morpholino)-1-butene (12.8 g, 0.09 mol) and triethylamine (12.6 mL, 0.09 mol) in dry tetrahydrofuran (120 mL) warmed at 70° C. under a nitrogen atmosphere. After 1.25 hours, the reaction was cooled to room temperature and nitro acetamide ammonium salt (12.0 g, 0.099 mol) was added, followed by the dropwise addition of acetic acid (11.4 mL, 0.20 mol). After stirring for 20–24 hours, the reaction was diluted with chloroform (150 mL) and the solution washed with water, 10% HCl, dried ($Na_2SO_4$) and filtered through a pad of charcoal. The solvent was removed and the residue triturated with cold methanol. The crystalline yellow product was filtered, rinsed with methanol and diethyl ether to give 8.01 g (31% yield), mp 157°–158° C.

Anal. calcd. for $C_{15}H_{16}N_2O_4$: C, 62.49; H, 5.59; N, 9.72. Found: C, 62.11; H, 5.29; N, 9.68.

Step B: Preparation of 3-amino-5-ethyl-6-hydroxymethylpyridin-2(1H)-one

A solution of 3-nitro-5-ethyl-6-benzyloxymethylpyridin-2(1H)-one (576 mg, 2.0 mmol) in tetrahydrofuran (15 mL) and methanol (15 mL) containing 10% palladium/charcoal (130 mg) was hydrogenated at an atmospheric pressure of hydrogen, monitoring the progress by tlc. Additional catalyst was added in 100 mg portions after day 2 and day 3. After 3–4 days, the catalyst was filtered and the solvents evaporated. The catalyst was vigorously washed with methanol/chloroform and combined solvents evaporated. The residue was triturated with methylene chloride and product collected by filtration to give 136 mg of 90% pure product. This material was used as is.

Step C: Preparation of 3-[2-(4,7-dichlorobenzoxazol-2-yl)methylamino]-5-ethyl-6-hydroxymethylpyridin-2(1H)-one A suspension of crude 3-amino-5-ethyl-6-hydroxymethylpyridin-2(1H)-one (134 mg, 0.80 mmol) and 2-iodomethyl-4,7-dichlorobenzoxazole (275 mg, 0.80 mmol, see Example 8) in acetonitrile (7 mL) containing diisopropylethylamine (0.96 mmol, 125 mg) was warmed at 50° C. for 4–5 hours. The precipitated product (165 mg) was removed by filteration and chromatographed on silica gel eluting with a 0–3.5% methanol/chloroform gradient. The appropriate fractions were combined, the solvents removed and the residue triturated with diethyl ether to give 95 mg (32% yield) of title compound, mp 193°–195° C.; $H^1$ NMR ($CDCl_3$, 300 MHz) δ 7.38 (2H,s), 6.50 (1H,s), 4.70 (2H,s), 4.49 (2H,s), 2.36 (2H, ABq, J=7.6 Hz), 1.10 (3H, t, J=7.6 Hz).

Anal. calcd. for $C_{16}H_{15}Cl_2N_3O_3$: C, 52.19; H, 4.11; N, 11.41. Found: C, 52.11; H, 4.08; N, 11.03.

EXAMPLE 8

Preparation of 2-iodomethyl-4,7-dichlorobenzoxazole

Step A: Preparation of 2-amino-3,6-dichlorophenol

A yellow solution of 2,5-dichloro-6-nitrophenol (10.0 g, 48.0 mmol) in ethanol (200 mL) and acetic acid (13.8 mL) at 0° C. was catalytically reduced in the presence of 5% platinum on charcoal (0.15 g) under an atmosphere of hydrogen (25 psi) for 1 hour in a Parr hydrogenator. The resultant colorless solution was filtered and concentrated under reduced pressure (15 torr). The residue was then dried under high vacuum (0.02 torr) overnight to yield 8.52 g (100%) of 2-amino-3,6-dichlorophenol.

Step B: Preparation of 2-iodomethyl-4,7-dichlorobenzoxazole

To a solution of 2-amino-3,6-dichlorophenol (23.91 g, 134 mmol) in methylene chloride (270 mL), solid ethyl iodoiminoacetate hydrogen chloride (202 mmol) is added. The resultant slurry is stirred at room temperature overnight, then filtered through a plug of Celite, and concentrated under reduced pressure (15 torr). The solid residue is subjected to column chromatoghraphy on silica gel (elution with chloroform). Collection and concentration of appropriate fractions yields 2-iodomethyl-4, 7-dichlorobenzoxazole.

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:

1. A method of preparing the compound

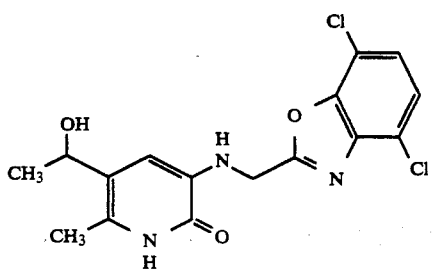

or a pharmaceutically acceptable ester thereof, comprising the steps of (1) providing a quantity of 3-[(4,7-dichlorobenzoxazol-2-yl)methyl]amino-5-ethyl-6-methyl-2-(1H)pyridinone,
(2) incubating the compound of step 1 with rat liver slices, and
(3) isolating the compound.

2. A method of preparing the compound

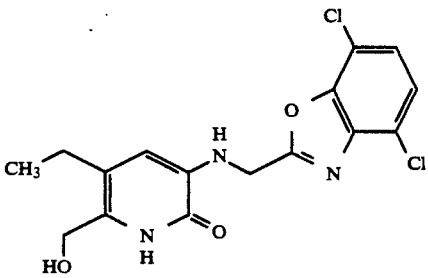

or a pharmaceutically acceptable ester thereof, comprising the steps of (1) providing a quantity of 3-[(4,7-dichlorobenzoxazol-2-yl)methyl] amino-5-ethyl-6-methyl-2-(1H)-pyridinone,
(2) incubating the compound of step 1 with rat liver slices, and
(3) isolating the compound.

* * * * *